United States Patent [19]
Gaus et al.

[11] Patent Number: 5,699,624
[45] Date of Patent: Dec. 23, 1997

[54] HIGH-TEMPERATURE EXTENSOMETER

[75] Inventors: Rainer Gaus, Holzkirchen; Stefan Zauner, Hausham; Günther Gesell, Stephanskirchen, all of Germany

[73] Assignee: Industrieanlagen-Betriebsgesellschaft mbH, Ottobrunn, Germany

[21] Appl. No.: 545,811
[22] PCT Filed: May 6, 1994
[86] PCT No.: PCT/EP94/01464
  § 371 Date: Mar. 25, 1996
  § 102(e) Date: Mar. 25, 1996
[87] PCT Pub. No.: WO94/27112
  PCT Pub. Date: Nov. 24, 1994

[30] Foreign Application Priority Data

May 8, 1993 [DE] Germany ............ 43 15 387.9

[51] Int. Cl.⁶ ...................................... G01B 5/30
[52] U.S. Cl. ........................................ 33/787; 73/795
[58] Field of Search ................... 33/787, 788, 789, 33/790; 73/766, 774, 795, 855, 767, 781

[56] References Cited

U.S. PATENT DOCUMENTS

| | | | |
|---|---|---|---|
| 2,588,630 | 3/1952 | Jackman | 33/790 |
| 4,884,456 | 12/1989 | Meline et al. | 73/826 |
| 5,015,825 | 5/1991 | Brindley | 374/49 |
| 5,083,465 | 1/1992 | Myers | 33/790 |
| 5,123,175 | 6/1992 | Van Der Kuur | 33/789 |

FOREIGN PATENT DOCUMENTS

| | | | |
|---|---|---|---|
| 2 611 046 A1 | 10/1988 | France. | |
| 2 616 901 A1 | 12/1988 | France. | |
| 28 16 444 A1 | 10/1979 | Germany. | |
| 38 03 926 A1 | 8/1988 | Germany. | |
| 37 14 185 A1 | 11/1988 | Germany. | |
| 8 700 084 | 8/1988 | Netherlands. | |
| 472749 | 9/1937 | United Kingdom | 33/787 |
| 2 220 493 | 1/1990 | United Kingdom. | |

OTHER PUBLICATIONS

Liu, et al., "Uniaxial Tensile Strain Measurement for Ceramic Testing at Elevated Temperatures: Requirements, Problems, and Solutions", *International Journal of High Technology Ceramics*, Bd. 4, 1988, pp. 161–179. No month.

Quesnel, et al., "Extensometer extender for conversion of room–temperature extensometers for high–temperature applications", *Review of Scientific Instruments*, Bd. 54, Nr. 2, Feb. 1983, NY, US, pp. 226–228.

Rohrbach, "Handbuch für experimentelle Spannungsanalyse", *VDI–Verlag GmbH*, 1989, pp. 560–565. No month.

*Primary Examiner*—Thomas B. Will
*Attorney, Agent, or Firm*—Marshall, O'Toole, Gerstein, Murray & Borun

[57] ABSTRACT

The invention relates to an apparatus for the one-dimensional, highly precise measurement of extension at the surfaces of hot specimens. The working range extends from normal temperature to about 1800° C., but measurements are also possible up to 2300° C. With respect to atmospheric pressure, the application range extends from vacuum up to pressures of several bar. The high-temperature extensometer in accordance with the invention is distinctly more cost-effective than previous extensometers for hot test specimens, despite its considerably larger measurement range.

7 Claims, 5 Drawing Sheets

HIGH-TEMPERATURE EXTENSOMETER

BACKGROUND OF THE INVENTION

The invention relates to a fluid-cooled extensometer for extension measurements preferably of hot test specimens and components; the application range lies between room temperature and about 2300° C. with a preferred working range up to about 1800° C. The extensometer in accordance with the invention can be employed under normal pressure as well as in high vacuum, and it is also possible to use it in the above-atmospheric pressure range. Normally the high-termperature extensometer in accordance with the invention is employed in an air atmosphere. However, it can also be used in any desired gaseous media, though in the case of corrosive or aggressive media the material chosen must have the appropriate characteristics. It is a fundamental feature of the invention that the extension measurements are possible regardless of relative movements of the specimen to be tested in the mm range; i.e., if such relative movements of the test specimen should occur during the measurement process, they are compensated inherently in all three spatial coordinates.

The previous state of the art is characterized by extensometers that do not perform this compensation. Furthermore, the previous extensometers do not ensure the high measurement accuracy, especially in the temperature ranges between about 1500° C. and 1800° C. Nor has it previously been possible to position the tips of the measurement probes with such precise reproducibility. In addition, the results of measurements with extensometers of the previous construction, apart from expensive special designs, are dependent on the atmospheric pressure.

SUMMARY OF THE INVENTION

It is therefore the object of the invention to provide an extensometer that compensates any movements of the test specimen in the mm range that may occur during the measurement process in all three spatial coordinates, that produces measurement results independent of the temperature of the test specimen up to about 1800° C. and of the ambient temperature up to about 150° C., and that enables exact, reproducible positioning of the probe tip.

DETAILED DESCRIPTION

Figure 1:
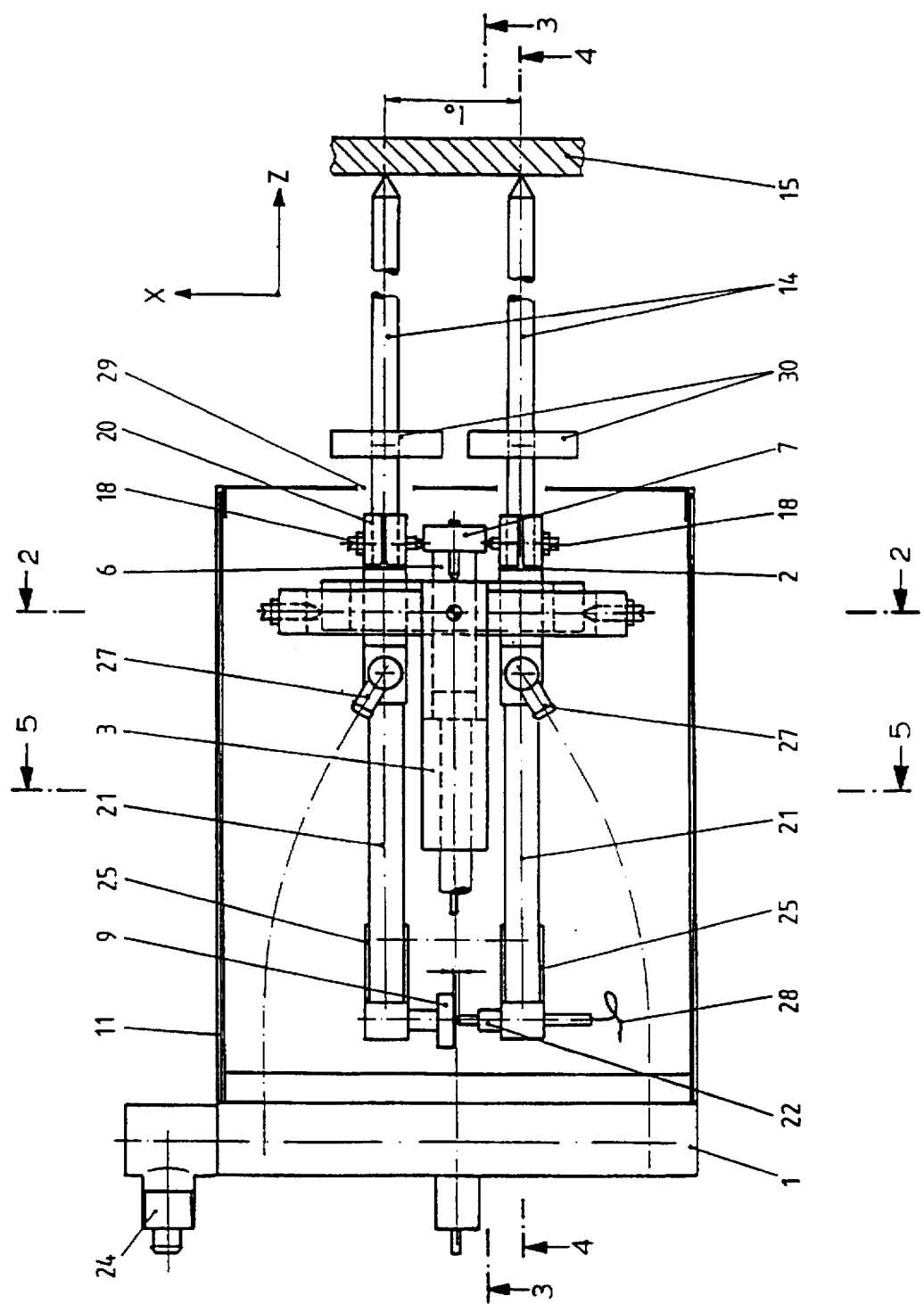
FIG. 1 is a schematic view of a high temperature extensometer according to the invention.
Figure 2:
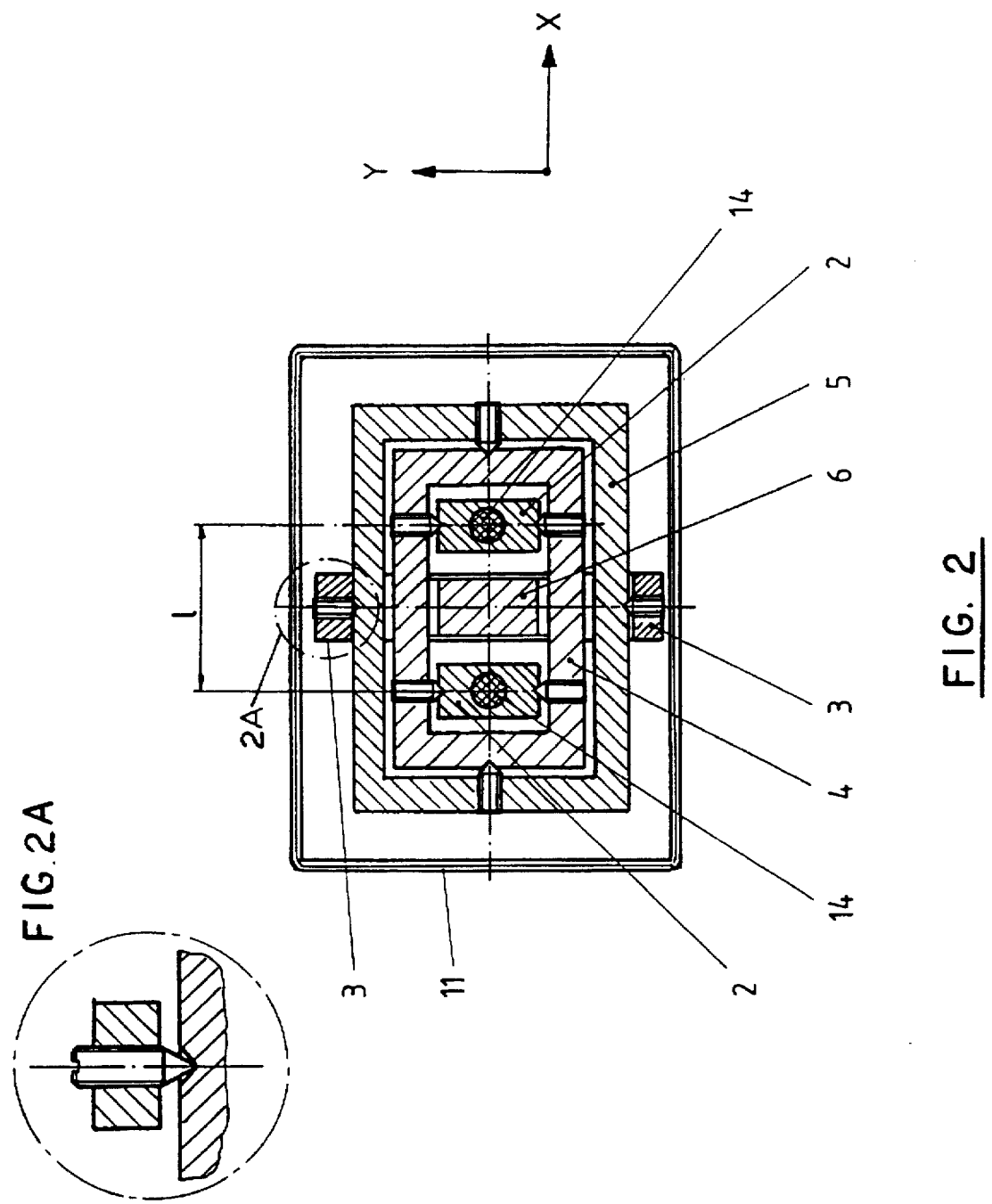
FIG. 2 is a sectional view along section line C—C of FIG. 1.
Figure 3:
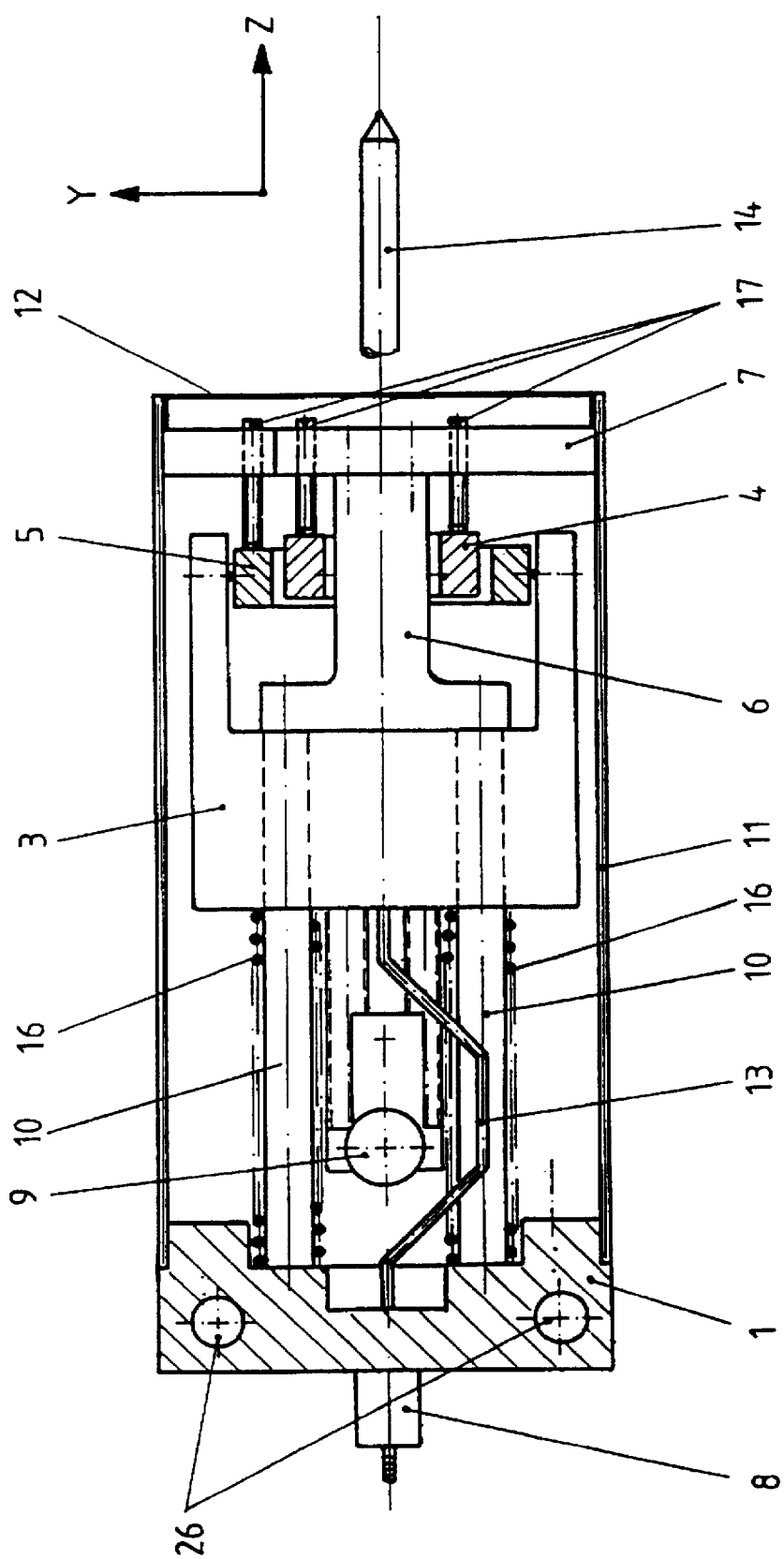
FIG. 3 is a sectional view along section line A—A of FIG. 1.
Figure 5:
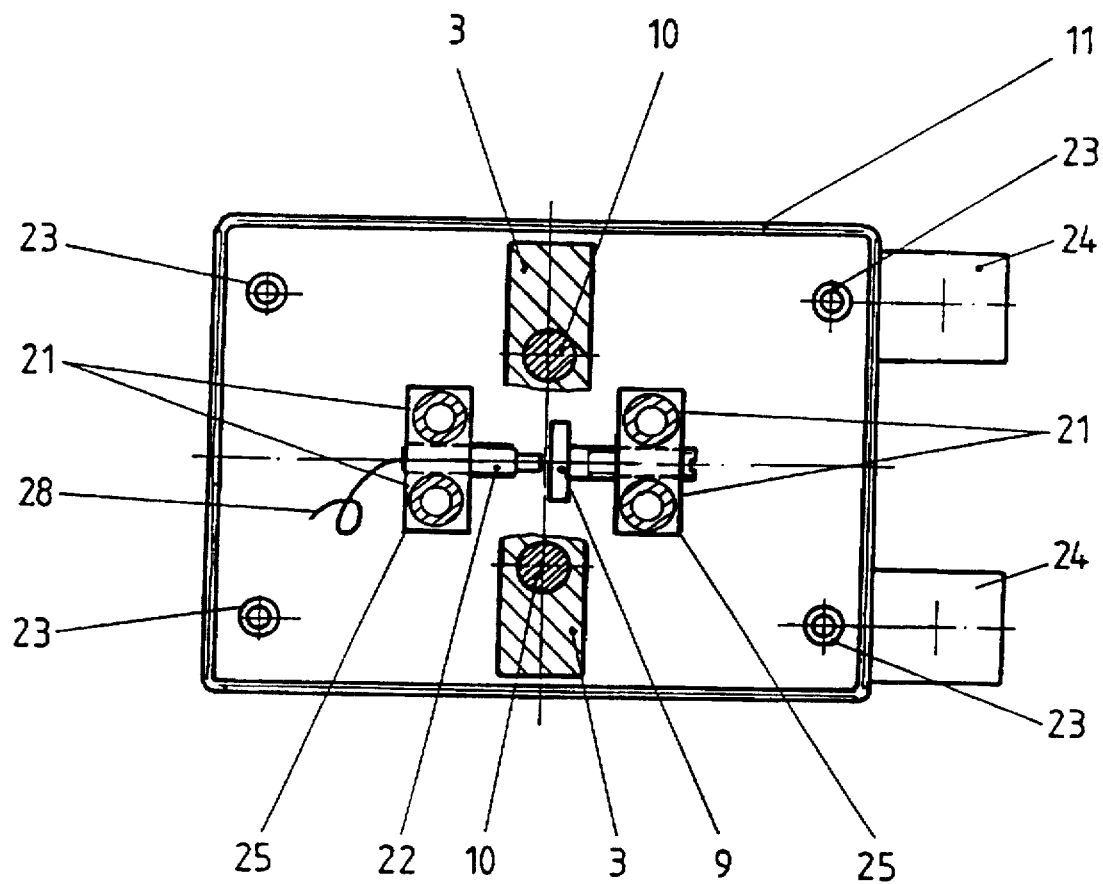
FIG. 5 is a sectional view along section line D—D of FIG. 1.

The two measurement probes 14, the tips of which make contact with the test specimen 15 (FIG. 1), are biaxially suspended on a gimbal mount in the frames 3, 4 and 5 (FIG. 2). In order to obtain relative movements of the two probes 14 only in a specified measurement direction X within the movement plane, or to permit such movements only there, each probe 14 is in turn independently gimbal-mounted within the frame 4 (FIG. 2). The outer frame 3 of the gimbal system is connected to a base plate 1 by a linear guide mechanism. here in the form of two shafts 10 arranged so that the frame 3 can slide on the shafts 10 in the long direction Z of the measurement apparatus (FIG. 3 and FIG. 5). Other linear guide means for the frame 3 are also possible, e.g. rollers. Two cylindrical pressure springs 16 press the frame 3 and hence the whole gimbal suspension including the probes 14 in the resting state, by way of the block 6, against the adjustable stop bolts 17, which are screwed into the stopping block 7. Independently thereof, the initial length $l_o$ (FIG. 1) in the resting state is adjusted by way of two additional stop bolts 18 and the stopping block 7. The probes 14 are likewise clamped by stop bolts 18 in the stopping block 7 and thereby fixed. In order to make the baseline length for the measurement $l_o$ in FIG. 1) variable in principle, exchangeable clamping devices 20 with smaller or larger bases are also provided.

When the extensometer is moved into contact with the test specimen, displacement of the frame 3 releases the stop bolts 17 and 18, so that the probes 14 become free to move in the measurement direction X and also have freedom of movement to allow spatial compensation of movements of the test specimen in the X-Y plane.

Figure 4:
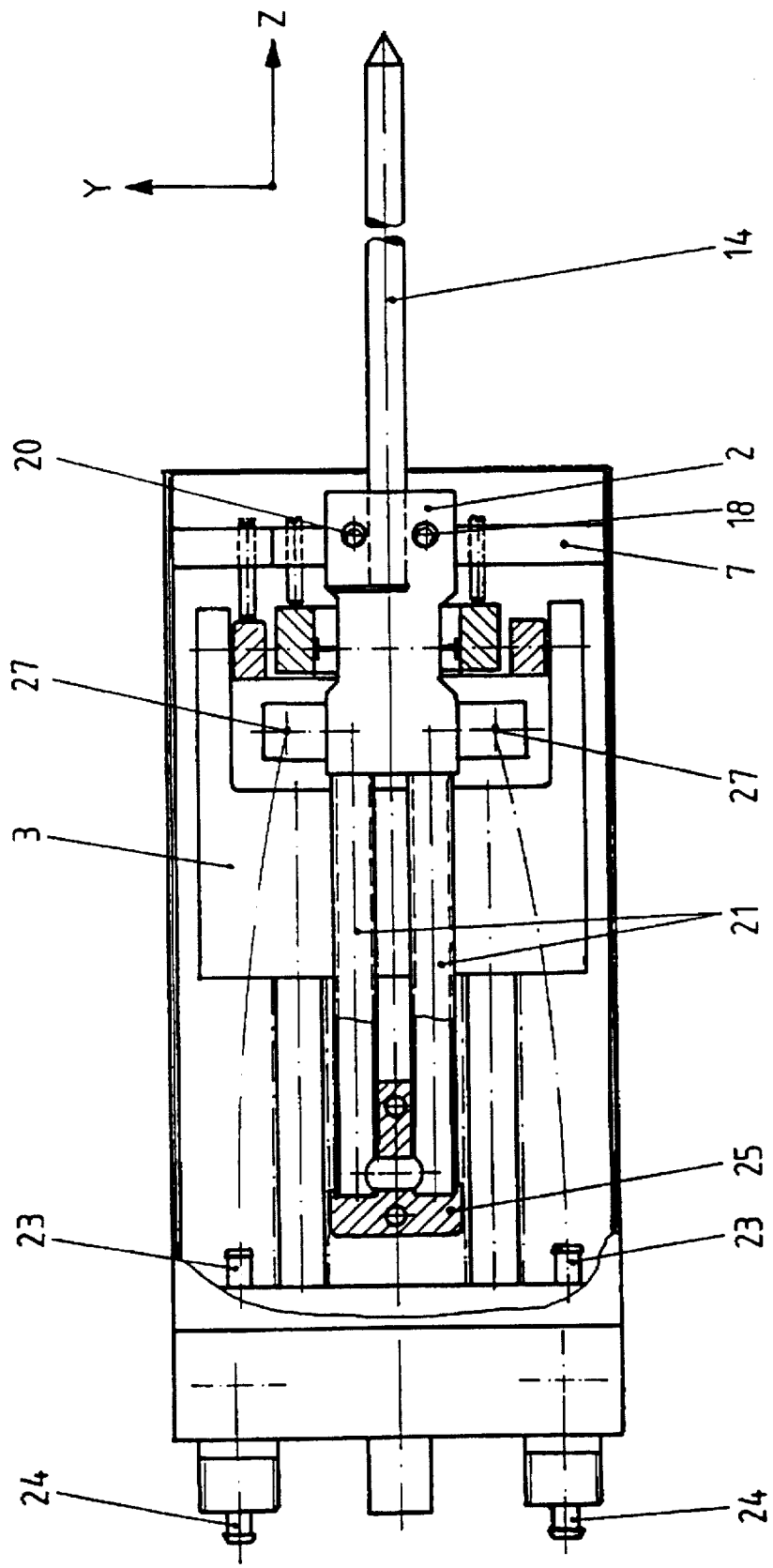
FIG. 4 is a sectional view along section line B—B of FIG. 1.

The probes 14 are clamped at their bases in the block 2 by the clamp mechanism 20 (FIG. 4). Also attached to block 2, but on the opposite side, are two pairs of tubes 21 that support the sensor 22 with counter-plate 9. The whole measurement system, including the probes 14, the gimbal suspension and the sensor 22, is so constructed that a movement of the probe tips in the X-Y plane causes a corresponding deflection of the sensor 22, but in the opposite direction of movement. However, a signal representing a measured extension is generated only when the distance between the tips of the probes changes. Expressly included in the invention are embodiments with more than two probes 14, for example with four measurement probes and two sensors 22 offset by 90° for the simultaneous measurement of extension in the X and the Y direction. A simplified design for two-dimensional extension measurement can also be implemented by a system with two probes, in which two sensors 22 are offset from one another by an angle, preferably 90°. Analogously, measurement in the Z direction is possible by means of a third sensor 22.

For the measurement system in accordance with the invention to be employed at high temperatures, effective cooling is required and is implemented as follows. Through one of the two external connections 24 (FIG. 4) the coolant, preferably water, is introduced into a cooling channel 26 (FIG. 3), from which it passes through two nipples 23, through flexible tubes (indicated in FIGS. 1 and 4) into two nipples 27 and thence through the tubes 21 and the sensor base 25. The coolant flows away by a corresponding route. The measurement system is contained within a housing 11. Because of the cooling as described above, in particular the sensor(s) 22 is (are) cooled in a controlled manner and protected by the housing from convection influences. The efficacious cooling of the base plate 1 is advantageous because the whole interior of the housing 11 is cooled as a result.

The signals generated by the sensor 22 are usefully recorded by way of a highly flexible miniature cable 28, which is led to the outside of the unit for subsequent signal processing.

To ensure reproducible adjustment of the measurement system, it is necessary to determine the force with which the probe tips press against the test specimen 15. In addition, it must be possible to monitor movements of the test specimen 15 in the Z direction. For this purpose the displacement of the block 3 with respect to the base plate 1 is measured, by a measurement rod 13 marked with a scale, which projects to a greater or lesser extent out of the sleeve 8. The measurement rod 13 is firmly attached to block 3, e.g. by soldering. The rod 13 is bent so that it will not contact the counter-plate 9 (FIG. 3).

The material of which the probes 14 are made must satisfy special requirements: the probes must be chemically compatible with the test specimen 15 at the application temperature, and they must be stiff and light. Therefore ceramic and fiber-ceramic materials are preferably used for this purpose, e.g. $Al_2O_3$ or C/C protected against oxidation.

To prevent radiation from the hot specimen 15 from entering directly through the probe openings 29 in the housing, a radiation shield 30 is attached to each probe 14.

In comparison with measurement systems according to the state of the art, the measurement system in accordance with the invention is distinguished by a significantly lower manufacturing price accompanied by a clear improvement in performance features.

We claim:

1. Extensometer measurement apparatus to measure thermally or mechanically induced extensions in the range of high temperatures of a test specimen up to about 2300° C., with a preferable working range from room temperature to about 1600° C., and with an application range of pressures from vacuum to about 100 bar, characterized by the combination of the following features:

an inner frame;

two inner blocks respectively spacially mounted in said inner frame separated by a distance l, said two inner blocks each mounted for independent rotation about their respective axes aligned with a reference direction Y in orthogonal directional axes references X, Y, Z;

two measurement probes coupled to a sensor for generating measurement signals, each measurement probe respectively mounted in one of said inner blocks;

an outer frame surrounding said inner frame, said inner frame rotatably mounted in said outer frame so as to be rotatable about said orthogonal directional axis reference X;

an outer block, said outer frame rotatably mounted in said outer block so as to be rotatable about said orthogonal directional axis reference Y;

a housing adapted for mounting said outer block therein;

a shaft mounted in said housing, said outer block movably mounted on said shaft for movement along said orthogonal directional axis reference Z; and means for supplying cooling liquid to said housing for cooling said sensor.

2. Extensometer measurement apparatus according to claim 1, wherein said sensor comprises a non-contact sensor.

3. Extensometer measurement apparatus according to claim 1, including adjustable stop bolts mounted in said housing to define specified starting positions of the probes in the orthogonal directional axis reference Z.

4. Extensometer measurement apparatus according to claim 1, including adjustable stopping block with adjustable stop bolts mounted in said housing to preset an initial distance l between said probes.

5. Extensometer measurement apparatus according to claim 3, including pressure springs mounted in said housing for urging said outer block against said stop bolts with said probes in said specified starting positions and for urging said probes against said test specimens during a measurement.

6. Extensometer measurement apparatus according to claim 5, including a measurement rod marked with a scale, said measurement rod coupled for movement with said probes to indicate the force exerted in the orthogonal directional axis reference Z by the probes contacting the test specimen.

7. Extensometer measurement apparatus according to claim 1, including a measurement rod marked with a scale, said measurement rod coupled for movement with said probes to indicate the force exerted in the orthogonal directional axis reference Z by the probes contacting the test specimen.

* * * * *